(12) United States Patent
Furukawa

(10) Patent No.: US 11,359,190 B2
(45) Date of Patent: Jun. 14, 2022

(54) THERMOLYSIN SOLUTION

(71) Applicant: AMANO ENZYME INC., Nagoya (JP)

(72) Inventor: Kazuhiro Furukawa, Kakamigahara (JP)

(73) Assignee: AMANO ENZYME INC., Nagoya (JP)

( * ) Notice: Subject to any disclaimer, the term of this patent is extended or adjusted under 35 U.S.C. 154(b) by 21 days.

(21) Appl. No.: 16/635,982

(22) PCT Filed: Jul. 30, 2018

(86) PCT No.: PCT/JP2018/028409
§ 371 (c)(1),
(2) Date: Jan. 31, 2020

(87) PCT Pub. No.: WO2019/026827
PCT Pub. Date: Feb. 7, 2019

(65) Prior Publication Data
US 2021/0147821 A1    May 20, 2021

(30) Foreign Application Priority Data

Jul. 31, 2017 (JP) .............................. JP2017-148221

(51) Int. Cl.
*C12N 9/54* (2006.01)

(52) U.S. Cl.
CPC ........ *C12N 9/54* (2013.01); *C12Y 304/24027* (2013.01)

(58) Field of Classification Search
CPC ............................................ C12Y 304/24027
USPC ....................................................... 435/212
See application file for complete search history.

(56) References Cited

U.S. PATENT DOCUMENTS

| | | |
|---|---|---|
| 5,801,022 A | 9/1998 | Navia |
| 6,140,475 A | 10/2000 | Margolin |
| 2002/0137156 A1 | 9/2002 | Margolin |
| 2003/0211127 A1 | 11/2003 | Margolin |
| 2004/0202643 A1 | 10/2004 | Margolin |
| 2006/0104935 A1 | 5/2006 | Margolin |
| 2006/0223156 A1 | 10/2006 | Margolin |
| 2010/0248326 A1 | 9/2010 | Hoelke |
| 2011/0146099 A1 | 6/2011 | Cardozo |
| 2012/0009651 A1 | 1/2012 | Estell |
| 2012/0244598 A1 | 9/2012 | Hoelke |
| 2014/0099698 A1 | 4/2014 | Estell |
| 2015/0337282 A1 | 11/2015 | Hoelke |
| 2016/0032266 A1 | 2/2016 | Estell |
| 2018/0251742 A1 | 9/2018 | Estell |

FOREIGN PATENT DOCUMENTS

| | | |
|---|---|---|
| JP | H6-46844 A | 2/1994 |
| JP | 2008-101196 A | 5/2008 |
| JP | 2008-283976 A | 11/2008 |
| JP | 2009-161623 A | 7/2009 |
| JP | 2010-051314 A | 3/2010 |
| JP | 2013-513717 A | 4/2013 |
| JP | 2016-052306 A | 4/2016 |
| WO | WO 1998/046732 A1 | 10/1998 |
| WO | WO 2010/105820 A1 | 9/2010 |
| WO | WO 2011/075357 A1 | 6/2011 |

OTHER PUBLICATIONS

Nohara et al, Media Selection for Refolding of Thermolysin by Use of Immobilized Preparation. Journal of Bioscience and Bioengineering vol. 89, No. 2, 188-192. 2000.*
Endo, S., Studies on Protease Produced by Themophilic Bacteria, Journal of Fermentation Technology, vol. 40, No. 7, pp. 346-353, 1962.
International Search Report, dated Oct. 9, 2018, for International Patent Application No. PCT/JP2018/028409.
Inouye et al., Effects of Salts on the Solubility of Thermolysin: A Remarkable Increase in the Solubility as Well as the Activity by the Addition of Salts without Aggregation or Dispersion of Thermolysin, Journal of Biochemistry, vol. 123, pp. 847-852, 1998.
Extended European Search Report dated Apr. 7, 2021 in European Application No. 18841723.2.
International Preliminary Report on Patentability dated Feb. 4, 2020 in International Application No. PCT/JP2018/028409.
Written Opinion dated Oct. 9, 2018 in International Application No. PCT/JP2018/028409.

* cited by examiner

*Primary Examiner* — Sheridan Swope
(74) *Attorney, Agent, or Firm* — Knobbe, Martens, Olson & Bear LLP

(57) ABSTRACT

A thermolysin solution has further improved stability as a result of the thermolysin solution containing thermolysin at a concentration that is 0.1 mg/mL or higher and the thermolysin solution having a pH that is adjusted to higher than 9.0. The thermolysin solution preferably has a pH in the range of 9.5-11.5.

6 Claims, 2 Drawing Sheets
Specification includes a Sequence Listing.

THERMOLYSIN SOLUTION

PRIORITY AND CROSS REFERENCE TO RELATED APPLICATIONS

This application is the U.S. National Stage Application under 35 U.S.C. § 371 of International Application No. PCT/JP2018/028409, filed Jul. 30, 2018, designating the U.S. and published as WO 2019/026827 A1 on Feb. 7, 2019, which claims the benefit of Japanese Patent Application No. JP 2017-148221, filed Jul. 31, 2017. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled LEX023003APCSEQLIST.txt, created and last modified on Jan. 30, 2020, which is 4,910 bytes in size. The information in the Electronic Sequence Listing is incorporated herein by reference in its entirety.

TECHNICAL FIELD

The present invention relates to a thermolysin liquid preparation. More specifically, the present invention relates to a thermolysin liquid preparation having improved stability.

BACKGROUND ART

Thermolysin is known, for example, as endoprotease (EC 3.4.24.27) derived from one of thermophilic bacteria that is *Geobacillus stearothermophilus* (Former: *Bacillus stearothermophilus*). The thermolysin is classified as metalloprotease and catalyzes a hydrolysis reaction using a protein as a substrate. The thermolysin has excellent heat resistance and exhibits an activity even at a high temperature near 80° C. particularly in the presence of a calcium salt.

It is widely known that thermolysin is stable at a pH of 5.0 to 8.0 or a pH of 6.0 to 9.0 (for example, see Patent Document 1 and Non-Patent Document 1), and it is also widely known that stability thereof is significantly degraded at a pH side higher than a pH of 6.0 to 9.0 (for example, see Non-Patent Document 1). For this reason, in preparation of a liquid containing thermolysin, preparation is performed usually at a pH of 5.0 to 9.0 in order to obtain stability.

For example, Patent Document 1 discloses that a pH of a liquid containing thermolysin is adjusted to 10.5 or higher to dissolve liquid crystal, salts are then allowed to coexist in a final concentration of 15 to 30% to decrease a pH to 5 to 8, preferably 6 to 7, and specifically up to 6.0, and thus a liquid product of thermolysin is produced. Further, Patent Document 2 discloses that thermolysin is allowed to coexist with a specific salt in the presence of a buffer salt capable of maintaining a pH in a range of 4.5 to 9 to stabilize thermolysin.

PRIOR ART DOCUMENTS

Patent Documents

Patent Document 1: Japanese Patent Laid-open Publication No. 6-46844
Patent Document 2: Japanese Patent Laid-open Publication No. 2010-051314

Non-Patent Document

Non-Patent Document 1: Journal of fermentation technology, vol. 40, no. 7, p. 346-353, 1962, FIG. 8

SUMMARY

As mentioned above, it is a general technical common knowledge that thermolysin is stable at a pH of 5.0 to 9.0. For this reason, in order to obtain a liquid containing thermolysin in a stable state, it is a main assumption that thermolysin is prepared at a pH of 5.0 to 9.0 as described above. As disclosed in Patent Documents 1 and 2, in order to obtain a liquid containing thermolysin in a stable state, examination on production processing and examination on conditions of a salt have been conducted, but the pH of the liquid containing thermolysin that is a final product is still adjusted to a category of 5.0 to 9.0. However, in these techniques, there are many restrictions in production and in composition, and these techniques are not suitable for industrial production.

Moreover, thermolysin also has a problem in that autodigestion occurs in a solution with a pH of 5.0 to 9.0. If the problem of autodigestion is tried to be avoided, restraint in the technical common knowledge that thermolysin is stabilized at a pH of 5.0 to 9.0 is extremely strong, and it is nothing else that stability of a liquid containing thermolysin is still examined at a pH of 5.0 to 9.0. That is, for those skilled in the art, there is not a room for examination on stability of the liquid containing thermolysin at a higher pH.

In this regard, an object of the present invention is to provide a thermolysin liquid preparation having further improved stability.

The present inventors have focused on a pH on which there has not been a room for examination hitherto for those skilled in the art upon examination of stability of a liquid containing thermolysin in a high concentration. As a result, surprisingly, the present inventors have found that by using a liquid containing thermolysin in a predetermined high concentration, the pH is adjusted to be higher than the pH which has been hitherto considered to be stable, so that stability can be improved. The present invention has been made based on these findings.

The present invention includes the following inventions.

Item 1. A thermolysin liquid preparation containing thermolysin in a concentration of 0.1 mg/mL or higher and having a pH adjusted to higher than 9.0.

Item 2. The thermolysin liquid preparation described in the item 1, in which the pH is 9.5 to 11.5.

Item 3. The thermolysin liquid preparation described in the item 1 or 2, in which the thermolysin liquid preparation contains sodium chloride in a concentration of 0.01 mM to 1 M.

Item 4. The thermolysin liquid preparation described in any one of the items 1 to 3, in which the thermolysin liquid preparation contains calcium chloride in a concentration of 0.01 mM to 1 M.

Item 5. The thermolysin liquid preparation described in the item 1 or 2, in which the thermolysin liquid preparation does not substantially contain a salt other than a buffer salt.

Item 6. A method for producing a thermolysin powder preparation, the method including: a step of drying the thermolysin liquid preparation described in any one of the items 1 to 5.

Item 7. A thermolysin dry preparation whose pH is higher than 9.0 when being dissolved in water to have a concentration of 2.5 w/v %.

Item 8. A method for improving stability of a thermolysin liquid preparation, the method including: preparing the thermolysin liquid preparation to contain thermolysin in a concentration of 0.1 mg/mL or higher and to have a pH adjusted to higher than 9.0.

According to the present invention, a thermolysin liquid preparation having further improved stability is provided.

DETAILED DESCRIPTION

[1. Thermolysin Liquid Preparation]

Figure 1:
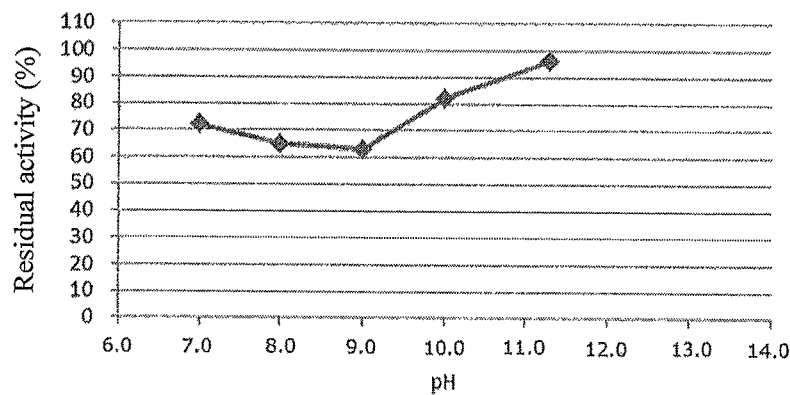
FIG. 1 is a graph showing a relation of stability (residual activity) with respect to a pH of a thermolysin liquid preparation obtained in Test Example 1.

The present invention provides a thermolysin liquid preparation. The thermolysin liquid preparation of the present invention contains thermolysin in water in a specific concentration and has a pH adjusted to a specific pH to be stabilized.

[1-1. Thermolysin]

Thermolysin is thermostable neutral metalloproteinase and exhibits a protease active effect at an optimum temperature of 65 to 85° C. and an optimum pH of 5.0 to 8.5. At the time of the protease active effect of the thermolysin, the N-terminal of a hydrophobic amino-acid residue is specifically cut. The thermolysin has one zinc ion for expressing enzyme activity at an active site and four calcium ions for maintaining a structure in the structure. The thermolysin is classified as EC number 3.4.24.27 and thermolysin registered as CAS registry number 9073-78-3 is known well.

Derivation of thermolysin contained in the thermolysin liquid preparation of the present invention is not particularly limited as long as thermolysin having the protease activity mentioned above can be produced. Examples of thermolysin-related bacteria include *Bacillus thermoproteolyticus, Geobacillus stearothermophilus, Bacillus amyloliquefaciens, Bacillus subtills, Bacillus cereus, Bacillus licheniformis*, and analogous bacteria thereof.

The amino acid sequence of thermolysin contained in the thermolysin liquid preparation of the present invention is not particularly limited as long as thermolysin has the protease activity mentioned above. From the viewpoint of more preferably obtaining stability at a high pH mentioned later, preferably, a protein having an amino acid sequence shown in SEQ ID NO: 1, and a protein which consists of an amino acid sequence having the deletion, substitution, insertion or addition of one or more of amino acids in the amino acid sequence shown in SEQ ID NO: 1 and which has the protease activity mentioned above are exemplified, and more preferably, a protein having an amino acid sequence shown in SEQ ID NO: 1 is exemplified. Further, as long as thermolysin has the protease activity mentioned above, the amino acid sequence of thermolysin may be an amino acid sequence having, for example, 70% or more, preferably 80% or more, more preferably 90% or more, and further preferably 95% or more identity with the amino acid sequence shown in SEQ ID NO: 1. Incidentally, the identity means a ratio (%) of the same overlapping amino acids relative to the total amino acid residue at the optimal alignment when two amino acid sequences are aligned using a mathematical algorithm known in the pertinent technical field (preferably, the algorithm is obtained by taking into consideration of introduction of a gap into one or both of the sequences for the optimal alignment).

The molecular weight of the thermolysin is, for example, 34000 to 38000 and preferably 34300 to 37500.

In the present invention, the thermolysin liquid preparation also contains a thermolysin decomposition product in addition to thermolysin which is not substantially decomposed. However, since the autodigestion of the thermolysin liquid preparation of the present invention is effectively suppressed, the amount of the thermolysin decomposition product is suppressed. Specifically, a ratio of thermolysin, which is not substantially decomposed, to the whole thermolysin (a sum of thermolysin, which is not substantially decomposed, and a thermolysin decomposition product) is, for example, 75% or more, preferably 80% or more, more preferably 85% or more, and further preferably 90% or more in terms of a detection amount (detection peak area in the chromatogram) with UV 280 nm by high-performance liquid chromatography. Incidentally, it is allowable that the thermolysin decomposition product includes, in addition to the decomposition product having the protease activity mentioned above, a decomposition product not having the activity. The protease activity of the thermolysin decomposition product is not particularly limited as long as the activity is detected.

[1-2. Thermolysin Concentration]

The thermolysin liquid preparation of the present invention contains thermolysin (referring to the whole thermolysin; that is, referring to a sum of thermolysin which is not substantially decomposed, and a thermolysin decomposition product) in a high concentration of 0.1 mg/mL or higher. From the viewpoint of more preferably obtaining stability of the thermolysin liquid preparation at a high pH, the whole thermolysin is contained in a concentration of preferably 0.2 mg/mL or higher, more preferably 0.4 mg/mL or higher, further preferably 0.8 mg/mL or higher, still more preferably 1.6 mg/mL or higher, further still more preferably 2.4 mg/mL or higher, and further still more preferably 3.2 mg/mL or higher. Further, the upper limit is not particularly limited, the concentration thereof may be a saturated concentration at a storage temperature of the thermolysin liquid preparation, but from the viewpoint of suppression of recrystallization of thermolysin, the upper limit is, for example, 6.6 mg/mL or lower, preferably 5.8 mg/mL or lower, more preferably 5.0 mg/mL or lower, and further preferably 4.2 mg/mL or lower. More specific examples of the concentration of thermolysin include 0.1 to 6.6 mg/mL, 0.2 to 6.6 mg/mL, 0.4 to 6.6 mg/mL, 0.8 to 6.6 mg/mL, 1.6 to 6.6 mg/mL, 2.4 to 6.6 mg/mL, 3.2 to 6.6 mg/mL, 0.1 to 5.8 mg/mL, 0.2 to 5.8 mg/mL, 0.4 to 5.8 mg/mL, 0.8 to 5.8 mg/mL, 1.6 to 5.8 mg/mL, 2.4 to 5.8 mg/mL, 3.2 to 5.8 mg/mL, 0.1 to 5.0 mg/mL, 0.2 to 5.0 mg/mL, 0.4 to 5.0 mg/mL, 0.8 to 5.0 mg/mL, 1.6 to 5.0 mg/mL, 2.4 to 5.0 mg/mL, 3.2 to 5.0 mg/mL, 0.1 to 4.2 mg/mL, 0.2 to 4.2 mg/mL, 0.4 to 4.2 mg/mL, 0.8 to 4.2 mg/mL, 1.6 to 4.2 mg/mL, 2.4 to 4.2 mg/mL, and 3.2 to 4.2 mg/mL.

The concentration of the whole thermolysin in the thermolysin liquid preparation of the present invention can also be derived from a protein amount and a thermolysin purity of the thermolysin liquid preparation. The protein amount can be measured by a known method. For example, the protein amount can be calculated using an absorptiometric method, a BCA method, a Biuret method, or the like. Preferably, a BCA method is exemplified. The purity of the whole thermolysin can be derived from a known measurement method. For example, as for the purity of the whole thermolysin, in chromatography methods, a method is exemplified in which the purity of the whole thermolysin is calculated from a sum of ratios of peak areas of thermolysin, which is not substantially decomposed, and a thermolysin decomposition product to the whole peak area in the chromatogram. For example, the method described in Test Example 4 is exemplified, but columns and separation conditions to be appropriately used can be set by those skilled in the art according to proteins to contaminate the thermolysin. In a case where the thermolysin liquid preparation does not substantially contain a protein other than the whole thermolysin, upon deriving the concentration of the whole thermolysin, the light absorbance at a wavelength of 280 nm of 1 mg/mL of the whole thermolysin in water (pH 7.0) can be set to 1.765. The purity of the whole thermolysin of the thermolysin liquid preparation is not particularly limited, but from the viewpoint of keeping stability and/or quality constant, as for the purity of detection with UV 280 nm by high-performance liquid chromatography, the purity is preferably 50% or more, more preferably 70% or more, further preferably 80% or more, further still more preferably 90% or more, and further still more preferably 95% or more.

[1-3. pH]

The thermolysin liquid preparation of the present invention has a pH adjusted to higher than 9.0. In the present invention, the pH is a value measured under a temperature condition of 25° C. The thermolysin liquid preparation of the present invention is prepared in the high concentration mentioned above, and thus, is stabilized in a high pH region higher than a pH of 9.0. Specific examples of the pH of the thermolysin liquid preparation include higher than 9.0 and 11.8 or lower, higher than 9.0 and 11.5 or lower, higher than 9.0 and 11.0 or lower, 9.5 to 11.8 (9.5 or higher and 11.8 or lower), 9.5 to 11.5, 9.5 to 11.0, 10.0 to 11.8, 10.0 to 11.5, 10.0 to 11.0, 10.5 to 11.8, 10.5 to 11.5, and 10.5 to 11.0. From the viewpoint of more favorably obtaining stability of the thermolysin liquid preparation, the pH is preferably 9.5 to 11.8, more preferably 9.5 to 11.5, further preferably 10.0 to 11.5, and still more preferably 10.5 to 11.0.

When the pH of the thermolysin liquid preparation of the present invention is adjusted to higher than 9.0, autodigestion is further suppressed as compared with the case of a pH lower than the above-described pH. Furthermore, in the case of a pH of 9.5 or higher at which more favorable stability is obtainable, the effect of suppression of autodigestion is higher, and in the case of a pH of 10.0 or higher at which further favorable stability is obtainable, autodigestion is rarely recognized.

[1-4. Salt]

The thermolysin liquid preparation of the present invention may contain a salt. Examples of the salt include a buffer salt and a salt other than the buffer salt.

As the buffer salt, a buffer salt which may be added in the production process of the thermolysin liquid preparation is used, and for example, in order to adjust the thermolysin concentration based on the light absorbance, buffer salts used for adjusting a thermolysin liquid to be adjusted in concentration to a predetermined pH are exemplified. Therefore, the buffer salt does not necessarily exhibit a buffering effect at the pH (higher than 9.0) of the thermolysin liquid of the present invention. Specific examples of the buffer salt include BES (N,N-bis(2-hydroxyethyl)-2-aminoethanesulfonic acid), tris(hydroxymethyl)aminomethane), bis-tris (bis(2-hydroxyethyl)amino-tris(hydroxymethyl)methane), bis-tris propane (1,3-bis(tris(hydroxymethyl)methylamino)propane), HEPES (N-(2-hydroxyethyl)-piperazine-N'-2-ethanesulfonic acid), MES (2-(N-morpholino)ethanesulfonic acid), MOPS (3-(N-morpholino)propanesulfonic acid), MOPSO (3-morpholino-2-hydroxypropanesulfonic acid), PIPES (piperazine-1,4-bis(2-ethanesulfonic acid)), TAPS (N-tris(hydroxymethyl)methyl-3-aminopropanesulfonic acid), TES (N-tris(hydroxymethyl)methyl-2-aminoethanesulfonic acid), TEA (triethanolamine), tricine(N-(2-hydroxy-1,1-bis(hydroxymethyl)ethyl)glycine), sodium acetate, sodium citrate, sodium borate, and sodium phosphate.

A salt other than the buffer salt is not particularly limited. For example, from the viewpoint of suppression of recrystallization of the thermolysin, sodium chloride is preferably exemplified as a salt other than the buffer salt. The content of sodium chloride in the thermolysin liquid preparation of the present invention is not particularly limited, but from the viewpoint of more favorably obtaining an effect of suppression of recrystallization, the content thereof is, for example, 0.01 mM to 1 M, preferably 1 mM to 1 M, more preferably 5 mM to 500 mM, and further preferably 10 mM to 400 mM. Further, for example, from the viewpoint of improving the stability of the thermolysin, calcium chloride is preferably exemplified as a salt other than the buffer salt. The content of calcium chloride in the thermolysin liquid preparation of the present invention is not particularly limited, but from the viewpoint of more favorably obtaining an effect of improvement of stability of the thermolysin, the content thereof is, for example, 0.01 mM to 1 M, preferably 0.01 mM to 200 mM, more preferably 0.05 mM to 100 mM, further preferably 0.1 mM to 50 mM, still more preferably 0.1 mM to 30 mM, further still more preferably 0.1 mM to 20 mM, and particularly preferably 0.1 to 10 mM.

Meanwhile, since the thermolysin liquid preparation of the present invention has a high pH, the thermolysin liquid preparation is stable even if not substantially containing a salt. Therefore, the thermolysin liquid preparation of the present invention may not substantially contain a salt. Examples of the salt which is not substantially contained include salts other than the buffer salt. As a salt other than the buffer salt in this case, examples are as mentioned above and include sodium chloride and calcium chloride. Incidentally, the expression "not substantially containing a salt" means that the concentration of the salt is, for example, 0.001 mM or less, preferably 0.0001 mM or less, more preferably 0.00001 mM or less, and particularly preferably 0 mM in terms of total amount.

[1-5. Other Components]

The thermolysin liquid preparation of the present invention may contain other components in addition to the aforementioned components. Examples of other components include, as a stabilizing agent, albumin, maltose, sucrose, trehalose, and glycerin. These stabilizing agents may be used singly or in combination of a plurality of kinds thereof.

Further, in the case of using the thermolysin liquid preparation of the present invention particularly in regenerative medicine areas, it is preferable that the thermolysin liquid preparation has fewer by-product derived from bacteria such as endotoxin. For example, it is preferable that the amount of endotoxin as measured by a known endotoxin test (so-called limulus method) is suppressed to be, for example, 1 EU/mg or less, preferably 0.1 EU/mg or less, more preferably 0.01 EU/mg or less, and further preferably 0.001 EU/mg or less that is a detection limit.

[1-6. Use Application]

The use application of the thermolysin liquid preparation of the present invention is not particularly limited as long as the protease activity is used. For example, the thermolysin liquid preparation may be used for analysis of a primary structure of a protein, for dispersing of tissue cells in the regenerative medicine area, or for food processing (for example, production of amino acid-based seasonings, production of peptides, an improvement in physical properties of proteins, an improvement in flavor of extracts, a decrease in allergen, or the like).

[2. Stability Improving Method of Thermolysin Liquid Preparation]

As mentioned above, by preparing a thermolysin liquid preparation to contain thermolysin in a concentration of 0.1 mg/mL or higher and to have a pH adjusted to higher than 9.0, stability of the thermolysin liquid preparation can be improved. Therefore, the present invention further provides a method for improving stability of a thermolysin liquid preparation, the method including: preparing the thermolysin liquid preparation to contain thermolysin in a concentration of 0.1 mg/mL or higher and to have a pH adjusted to higher than 9.0. In this stability improving method, components to be used in the thermolysin liquid preparation, the use amount, the activity, the use application of the thermolysin liquid preparation, and the like are as described in the section of "1. Thermolysin liquid preparation" mentioned above.

[3. Method for Producing Thermolysin Liquid Preparation]

A method for producing a thermolysin liquid preparation of the present invention is not particularly limited. Thermolysin serving as a starting material to be used in the method for preparing a thermolysin liquid preparation of the present invention can be appropriately produced from origin organism described in "1-1. Thermolysin" mentioned above by those skilled in the art according to a known method. For example, a method is exemplified in which a proper culture medium (for example, a culture medium or the like containing liquefied starch, soybean meal, or casein) is used, the culture medium is heat-sterilized (for example, for about 30 minutes) and then cooled (for example, up to about 55° C.), an inoculum is then ingested and subjected to aerated and agitated culture at 53 to 55° C. to thereby produce thermolysin (specifically, the method described in Non-Patent Document 1 can be referred to). Further, a method is also exemplified in which a vector having a thermolysin gene, which is cloned from the aforementioned thermolysin-related bacteria, being incorporated is transfected to the genus *Bacillus* or the genus *Escherichia coli* by using a genetic recombination technology, and then the thermolysin gene is expressed (for example, the method described in Japanese Patent Laid-open Publication No. 3-232494 can be referred to). Incidentally, in the case of obtaining thermolysin derived from *Geobacillus stearothermophilus*, the thermolysin can be produced using a deposited strain of accession number No. NBRC12550, No. NBRC12983, No. NBRC13737, No. NBRC100862, or the like. Further, commercially available thermolysin (for example, thermolysin provided from Amano Enzyme Inc.) may be used as a starting material.

Thermolysin is first suspended, for example, in an aqueous solution for suspension and can be prepared as a thermolysin suspension. As the aqueous solution for suspension, water and a buffer solution are exemplified, and a buffer solution is preferably exemplified. The buffer solution can be appropriately selected by those skilled in the art according to a pH, which has to be adjusted, of the thermolysin suspension, and for example, an aqueous solution of the aforementioned buffer salt is exemplified. The pH of the suspension is not particularly limited, but for example, may be adjusted in a neutral region, specifically, 7.0 to 8.0. As for the thermolysin suspension, the amount of thermolysin in the suspension can be adjusted by measuring a light absorbance and adjusting a liquid volume and/or the amount of thermolysin so as to obtain a predetermined light absorbance. More specifically, for example, by setting the light absorbance in a wavelength of 280 nm of 1 mg/mL of the whole thermolysin in water (pH 7.0) to 1.765 and adjusting the pH of the suspension to 7.0, the amount of thermolysin can be adjusted so as to obtain a predetermined light absorbance with which the thermolysin concentration of the present invention described in "1-2. Thermolysin concentration" mentioned above is provided.

The pH of the thermolysin suspension is increased using a base and is adjusted to be a pH of higher than 9.0. Specifically, the pH is adjusted to pH described in "1-3. pH" mentioned above (preferably 10.0 to 11.5 and more preferably 10.5 to 11.0). As the base, a strong base such as potassium hydroxide, sodium hydroxide, and/or calcium hydroxide and/or ammonia and the like can be used in an aqueous solution state. Further, for final adjustment of the pH, acids may be appropriately used in combination. Examples of acids include inorganic acids such as hydrochloric acid and/or sulfuric acid and/or organic acids such as acetic acid and/or formic acid. According to this, a crudely purified thermolysin solution having an adjusted pH is obtained.

Alternatively, instead of increasing of the pH after thermolysin is suspended in an aqueous solution for suspension, thermolysin may be first dissolved directly in a basic aqueous solution having a pH adjusted to higher than 9.0, specifically, to pH described in "1-3. pH" mentioned above (preferably 10.0 to 11.5 and more preferably 10.5 to 11.0). As the basic aqueous solution, an aqueous solution of a strong base such as potassium hydroxide, sodium hydroxide, or calcium hydroxide and/or ammonia and the like is exemplified. Further, for final adjustment of the pH of the basic aqueous solution, acids may be appropriately used in combination. Examples of acids include inorganic acids such as hydrochloric acid and/or sulfuric acid and/or organic acids such as acetic acid and/or formic acid. According to this, a crudely purified thermolysin solution having an adjusted pH is obtained.

The crudely purified thermolysin solution having the adjusted pH mentioned above can be obtained without any changes as a thermolysin liquid preparation, but as necessary, the crudely purified thermolysin solution may be subjected to a refining treatment of removing an insoluble matter or miscellaneous bacteria by filtration or the like. A specific method for filtration is not particularly limited, and examples thereof include microfiltration and ultrafiltration.

[4. Method for Producing Thermolysin Dry Preparation, and Thermolysin Dry Preparation]

The present invention also provides a method for producing a thermolysin dry preparation. In the method for producing a thermolysin dry preparation of the present invention, the aforementioned thermolysin liquid preparation is provided to a drying step to thereby produce a thermolysin dry preparation. The thermolysin liquid preparation of the present invention is stable in a liquid state; however, it was found that even in an aspect in which the liquid having a high pH (higher than 9.0) is directly dried to obtain a dry preparation once, excellent activity can be exhibited when the dry preparation is dissolved in water again at the time of use. That is, it was found that the thermolysin liquid preparation of the present invention is not adversely affected by the activity of thermolysin in the drying step. The drying method is not particularly limited, and examples thereof include a freeze-dry method, a spray-dry method, and a decompressed concentration-drying method. Since the volume or weight of the obtained thermolysin dry preparation is decreased, the thermolysin dry preparation is more preferable than a liquid preparation in terms of conveyance and storage. The form of the thermolysin dry preparation is not particularly limited, and examples thereof include a powder, a subtle granule, a granule, and a tablet.

That is, the present invention also provides a thermolysin dry preparation. The thermolysin dry preparation of the present invention is obtained by drying the aforementioned thermolysin liquid preparation. Specifically, regarding the thermolysin dry preparation of the present invention, when the thermolysin dry preparation is dissolved in water to have a concentration of 2.5 w/v %, the pH of the aqueous solution is higher than 9.0; specifically, higher than 9.0 and 11.8 or lower, higher than 9.0 and 11.5 or lower, higher than 9.0 and 11.0 or lower, 9.5 to 11.8 (9.5 or higher and 11.8 or lower), 9.5 to 11.5, 9.5 to 11.0, 10.0 to 11.8, 10.0 to 11.5, 10.0 to 11.0, 10.5 to 11.8, 10.5 to 11.5, and 10.5 to 11.0; preferably 9.5 to 11.5, more preferably 10.0 to 11.5, and further preferably 10.5 to 11.0.

The activity value of the thermolysin dry preparation of the present invention is not particularly limited since the activity value varies depending on salts or the like to be contained, but the activity value per unit mass is, for example, 100 PU/mg or more, preferably 500 PU/mg or more, more preferably 1000 PU/mg or more, further preferably 2000 PU/mg or more, and still more preferably 3000 PU/mg or more. Further, the upper limit is not particularly limited, and is, for example, 15000 PU/mg or less, preferably 12000 PU/mg or less, more preferably 10000 PU/mg or less, and further preferably 8000 PU/mg or less. Specific examples of the activity value per unit mass of the thermolysin dry preparation include 100 to 15000 PU/mg, 500 to 15000 PU/mg, 1000 to 15000 PU/mg, 2000 to 15000 PU/mg, 3000 to 15000 PU/mg, 100 to 12000 PU/mg, 500 to 12000 PU/mg, 1000 to 12000 PU/mg, 2000 to 12000 PU/mg, 3000 to 12000 PU/mg, 100 to 10000 PU/mg, 500 to 10000 PU/mg, 1000 to 10000 PU/mg, 2000 to 10000 PU/mg, 3000 to 10000 PU/mg, 100 to 8000 PU/mg, 500 to 8000 PU/mg, 1000 to 8000 PU/mg, 2000 to 8000 PU/mg, and 3000 to. The activity value can be measured by a casein decomposition method. In the casein decomposition method, a hydrolysis reaction is performed at a pH of 7.5 and 35° C. using casein as a substrate, a non-protein substance to be produced is measured by a Folin colorimetric method, and the amount of enzyme liberating the non-protein substance corresponding to 1 μg of tyrosine for 1 minute is calculated as 1 PU (Protease Unit). The thermolysin dry preparation of the present invention exhibits excellent activity after being dissolved in water since the thermolysin dry preparation is obtained from a thermolysin liquid preparation which is not affected by the thermolysin activity in the drying step.

EXAMPLES

Hereinafter, the present invention will be described in more detail by means of Examples, but the present invention is not limited to these Examples. In the following description, a spectrophotometer (manufactured by SHIMADZU CORPORATION, Model No. UV-2500PC) was used in measurement of the light absorbance ($A_{280}$) in a wavelength of 280 nm. Further, the light absorbance in a wavelength of 280 nm in 1 mg/mL of water (pH 7.0) of thermolysin was set to 1.765.

Test Example 1

A thermolysin liquid preparation was prepared by the following method.

1. 0.7 g of thermolysin (Amano Enzyme Inc.) was suspended in 100 mL of an aqueous solution with a pH of 7.0 containing 30 mM of HEPES, 9 mM of calcium chloride, and 360 mM of sodium chloride.

2. The obtained suspension was subjected to liquid volume adjustment to have $A_{280}$=6.9, thereby adjusting a thermolysin concentration.

3. The pH of the thermolysin solution whose concentration had been adjusted was adjusted to 11.3 by using a 1 N sodium hydroxide aqueous solution under 25° C. environment, and then the pH was adjusted to 7.0, 8.0, 9.0, 10.0, and 11.0, respectively, by using a 1 N acetic acid aqueous solution. According to this, thermolysin liquid preparations with pHs of 7.0, 8.0, 9.0, 10.0, and 11.0 were obtained. The obtained thermolysin liquid preparations did not substantially contain a protein other than thermolysin, and thus the thermolysin concentration was obtained from a light absorbance of 280 nm, and as a result, was 3.7 mg/mL.

4. The thermolysin liquid preparation with each pH was left to stand still at 25° C. for 7 hours under the adjusted pH environment, and then stability was examined.

5. The activity of the thermolysin liquid preparation with each pH after still standing was measured using a casein decomposition method. Incidentally, as for the activity of the thermolysin liquid preparation with each pH after still standing, the obtained activity value was calculated with a relative value in which the activity value before still standing, which had been measured in advance, was regarded as 100%, and then the relative value was calculated as residual activity (%).

Incidentally, in the casein decomposition method, a hydrolysis reaction was performed at a pH of 7.5 and 35° C. using casein as a substrate, a non-protein substance to be produced was measured by a Folin colorimetric method, and the amount of enzyme liberating the non-protein substance corresponding to 1 μg of tyrosine for 1 minute was calculated as 1 PU (Protease Unit).

The results are presented in FIG. 1. In the thermolysin liquid preparations with pHs of 7.0, 8.0, and 9.0, the activity was degraded as the pH was increased. On the other hand, in the thermolysin liquid preparations with pHs of 10.0 and 11.0, a significant improvement in stability was recognized. Of these, the thermolysin liquid preparation with a higher pH, that is, pH of 11.0 had higher stability.

Test Example 2

A thermolysin liquid preparation was prepared by the following method.

1. 0.7 g of thermolysin (Amano Enzyme Inc.) was suspended in 100 mL of 30 mM HEPES buffer solution (pH 7.0).

2. The obtained suspension was subjected to liquid volume adjustment to have $A_{280}$=6.9, thereby adjusting a thermolysin concentration.

3. The pH of the thermolysin solution whose concentration had been adjusted was adjusted to 11.3 by using a 1 N sodium hydroxide aqueous solution under 25° C. environment, and then the pH was adjusted to 9.5, 10.0, 10.5, 11.0, 11.5, 12.0, and 12.5, respectively, by using a 1 N sodium hydroxide aqueous solution or a 1 N acetic acid aqueous solution. According to this, thermolysin liquid preparations with pHs of 9.5, 10.0, 10.5, 11.0, 11.5, 12.0, and 12.5 were obtained. The obtained thermolysin liquid preparations did not substantially contain a protein other than thermolysin, and thus the thermolysin concentration was obtained from a light absorbance of 280 nm, and as a result, was 3.7 mg/mL.

4. The thermolysin liquid preparation with each pH was left to stand still at 25° C. for 3 hours under the adjusted pH environment, and then stability was examined.

5. The activity of the thermolysin liquid preparation with each pH after still standing was measured using a casein decomposition method. Incidentally, as for the activity of the thermolysin liquid preparation with each pH after still standing, the obtained activity value was calculated with a relative value in which the activity value before still standing, which had been measured in advance, was regarded as 100%, and then the relative value was calculated as residual activity (%).

Figure 2:
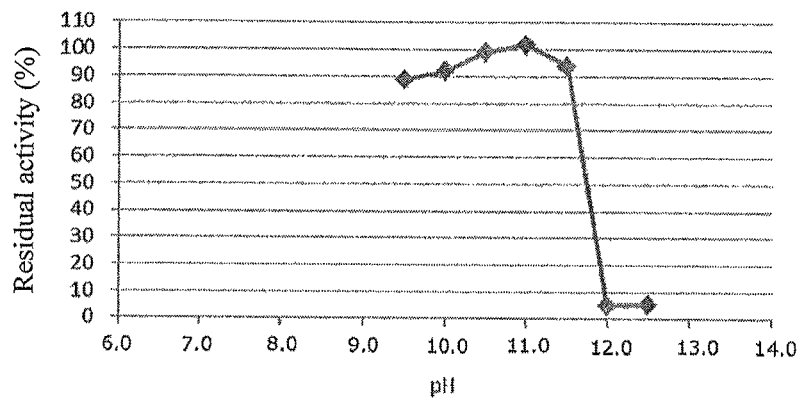
FIG. 2 is a graph showing a relation of stability (residual activity) with respect to a pH of a thermolysin liquid preparation obtained in Test Example 2.

The results are presented in FIG. 2. In the thermolysin liquid preparations with pHs of 9.5, 10.0, 10.5, and 11.0, similarly to FIG. 1 of Test Example 1, a tendency that stability is improved as the pH becomes higher was recognized. Further, the thermolysin liquid preparation with a pH of 11.5 also had high stability. On the other hand, the thermolysin liquid preparation with pHs of 12.0 and 12.5 did not have stability.

Test Example 3

A thermolysin liquid preparation was prepared by the following method.

1. 0.02 g to 1.0 g of thermolysin (Amano Enzyme Inc.) was suspended in 100 mL of 30 mM HEPES buffer solution (pH 7.0). 2. The obtained suspension was subjected to liquid volume adjustment to have $A_{280}$=0.2, 0.8, 3.0, 6.9, and 9.3, thereby adjusting a thermolysin concentration.

3. The pH of the thermolysin solution whose concentration had been adjusted was adjusted to 11.3 by using a 1 N sodium hydroxide aqueous solution under 25° C. environment, and then the pH was adjusted to 9.5 and 11.5, respectively, by using a 1 N sodium hydroxide aqueous solution or a 1 N acetic acid aqueous solution. According to this, thermolysin liquid preparations with pHs of 9.5 and 11.5 were obtained. The obtained thermolysin liquid preparations did not substantially contain a protein other than thermolysin, and thus the thermolysin concentrations were obtained from a light absorbance of 280 nm, and as a result, were 0.1 mg/mL, 0.4 mg/mL, 1.6 mg/mL, 3.7 mg/mL, and 5.0 mg/mL, respectively.

4. The thermolysin liquid preparation with each thermolysin concentration and each pH was left to stand still at 25° C. for 7 hours under the adjusted pH environment, and then stability was examined.

5. The activity of each thermolysin liquid preparation after still standing was measured using a casein decomposition method. Incidentally, as for the activity of each thermolysin liquid preparation after still standing, the obtained activity value was calculated with a relative value in which the activity value before still standing, which had been measured in advance, was regarded as 100%, and then the relative value was calculated as residual activity (%).

Figure 3:
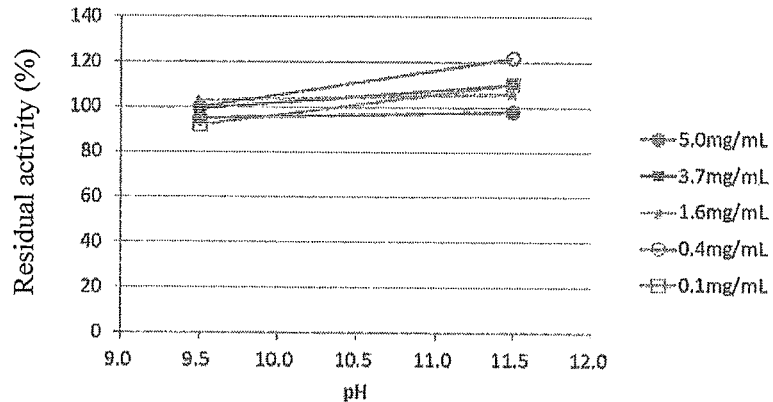
FIG. 3 is a graph showing a relation of stability (residual activity) with respect to pHs of thermolysin liquid preparations having various concentrations obtained in Test Example 3.

The results are presented in FIG. 3. Even in a case where the thermolysin concentration is any of 0.1 mg/mL, 0.4 mg/mL, 1.6 mg/mL, 3.7 mg/mL, and 5.0 mg/mL, the pH was 9.5 and 11.5, and similarly to FIG. 2 of Test Example 2, the thermolysin liquid preparation had high stability.

Test Example 4

Each thermolysin liquid preparation obtained in Test Example 1 was provided to HPLC under the following conditions and the degree of autodigestion was measured.
<HPLC Conditions>

Column: YMC-triart C18 (150×4.6 mm) (YMC CO., LTD.)

A buffer: 0.1% trifluoroacetic acid in ultrapure water

B buffer: 0.1% trifluoroacetic acid in acetonitrile

Gradient condition (percentage of B buffer with respect to A buffer): 0 to 60% (0 to 20 minutes), 100% (20 to 25 minutes)

Flow rate: 1 mL/min

Detector: ultraviolet absorptiometer (280 nm)

Figure 4:
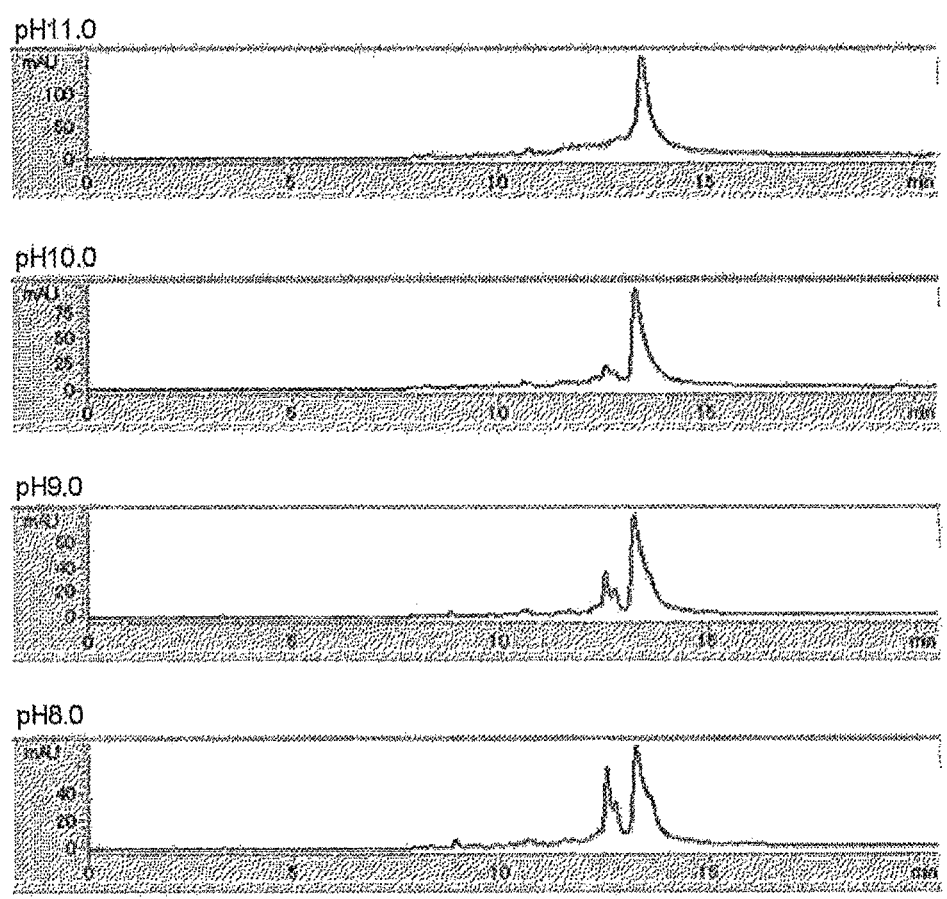
FIG. 4 shows HPLC chromatograms of thermolysin liquid preparations with respective pHs obtained in Test Example 4.

The results are presented in FIG. 4. In FIG. 4, a peak at 13 to 14 minutes corresponds to thermolysin which is not substantially decomposed and a peak at 12 to 13 minutes corresponds to a thermolysin decomposition product. Results obtained by deriving the ratio of each of thermolysin, which is not substantially decomposed, and the thermolysin decomposition product to the whole thermolysin (that is, a sum of thermolysin, which is not substantially decomposed, and a thermolysin decomposition product) based on a detection amount (detection peak area in the chromatogram) with UV 280 nm are presented in Table 1. From these results, it was possible to adjust the ratio of thermolysin, which is not substantially decomposed, to 79% or more by adjusting the pH of the thermolysin liquid preparation to higher than 9.0. That is, it was possible to effectively suppress autodigestion of thermolysin.

TABLE 1

| pH | Thermolysin which is not substantially decomposed (%) | Thermolysin decomposition product (%) |
|---|---|---|
| 11.0 | 94 | 6 |
| 10.0 | 90 | 10 |
| 9.0 | 79 | 21 |
| 8.0 | 65 | 35 |

Test Example 5

A thermolysin dry preparation was prepared by the following method.

1. 0.7 g of thermolysin (Amano Enzyme Inc.) was suspended in 100 mL of an aqueous solution with a pH of 7.0 containing 30 mM of HEPES, 9 mM of calcium chloride, and 360 mM of sodium chloride.

2. The obtained suspension was subjected to liquid volume adjustment to have $A_{280}$=6.9, thereby adjusting a thermolysin concentration.

3. The pH of the thermolysin solution whose concentration had been adjusted was adjusted to 11.3 by using a 1 N sodium hydroxide aqueous solution under 25° C. environment, and then the pH was adjusted to 8.0, 9.0, 10.0, and 11.0, respectively, by using a 1 N acetic acid aqueous solution. According to this, thermolysin liquid preparations with pHs of 8.0, 9.0, 10.0, and 11.0 were obtained.

4. The thermolysin liquid was provided to microfiltration to remove an insoluble matter.

5. The activity of the obtained thermolysin liquid preparation was measured using a casein decomposition method.

6. The thermolysin liquid preparation was freeze-dried to obtain a thermolysin dry preparation.

7. The activity of the obtained thermolysin dry preparation was measured using a casein decomposition method. The measurement was performed to a thermolysin aqueous solution obtained by dissolving the thermolysin dry preparation in water to have a concentration of 2.5 w/v %. (Incidentally, when the dry preparation obtained from the thermolysin liquid preparation with pH of 11 was dissolved in water to have the aforementioned concentration, the pH of the thermolysin aqueous solution became 11. Similarly, when the dry preparations obtained from the thermolysin liquid preparations with pHs of 10, 9, and 8 were dissolved in water to have the aforementioned concentration, the pHs of the thermolysin aqueous solutions became 10, 9, and 8, respectively.)

The obtained activity value was calculated with a relative value in which the activity value of the thermolysin liquid preparation was regarded as 100%, and the relative value was calculated as a residual activity (%).

The results are presented in Table 2. As described above, even in any of the thermolysin dry preparations, favorable activity was obtained in the case of dissolving the thermolysin dry preparation in water again. Therefore, even when the thermolysin liquid preparation of the present invention was dried once to obtain a thermolysin dry preparation, it was confirmed that favorable activity was obtained in the case of dissolving the thermolysin dry preparation in water again.

TABLE 2

| pH | Residual activity after freeze-drying (%) |
|---|---|
| 8.0 | 98 |
| 9.0 | 100 |
| 10.0 | 98 |
| 11.0 | 97 |

What is claimed is:

1. A thermolysin liquid preparation comprising thermolysin in a concentration of 0.1 to 5.0 mg/mL and having a pH adjusted to higher than 9.0, the thermolysin liquid preparation not containing an added salt other than a buffer salt.

2. The thermolysin liquid preparation according to claim 1, wherein the pH is 9.5 to 11.5.

3. The thermolysin liquid preparation according to claim 1, wherein the thermolysin liquid preparation contains sodium chloride in a concentration of 0.01 mM to 1 M.

4. A method for producing a thermolysin dry preparation, the method comprising: a step of drying the thermolysin liquid preparation according to claim 1.

5. A method for preparing a stable thermolysin liquid preparation at a concentration of 0.1 mg/mL or higher and a pH of 9.5 to 11.5 said preparation not containing an added salt other than a buffer salt, wherein the thermolysin retains at least 90% activity after storage at 25° C. for 3 hours, compared to the thermolysin activity prior to storage of the preparation.

6. The method of claim 5 wherein the thermolysin retains at least 90% activity after storage at 25° C. for 7 hours, compared to the thermolysin activity prior to storage of the preparation.

* * * * *

SEQUENCE LISTING

<160> NUMBER OF SEQ ID NOS: 1

<210> SEQ ID NO 1
<211> LENGTH: 536
<212> TYPE: PRT
<213> ORGANISM: Bacillus thermoproteolyticus

<400> SEQUENCE: 1

```
Met Lys Met Lys Met Lys Leu Ala Ser Phe Gly Leu Ala Ala Gly Leu
1               5                   10                  15

Ala Ala Gln Val Phe Leu Pro Tyr Asn Ala Leu Ala Ser Thr Glu His
            20                  25                  30

Val Thr Trp Asn Gln Gln Phe Gln Thr Pro Gln Phe Ile Ser Gly Asp
        35                  40                  45

Leu Leu Lys Val Asn Gly Thr Ser Pro Glu Glu Leu Val Tyr Gln Tyr
    50                  55                  60

Val Glu Lys Asn Glu Asn Lys Phe Lys Phe His Glu Asn Ala Lys Asp
65                  70                  75                  80

Thr Leu Gln Leu Lys Glu Lys Lys Asn Asp Asn Leu Gly Phe Thr Phe
                85                  90                  95

Met Arg Phe Gln Gln Thr Tyr Lys Gly Ile Pro Val Phe Gly Ala Val
            100                 105                 110

Val Thr Ser His Val Lys Asp Gly Thr Leu Thr Ala Leu Ser Gly Thr
        115                 120                 125

Leu Ile Pro Asn Leu Asp Thr Lys Gly Ser Leu Lys Ser Gly Lys Lys
    130                 135                 140

Leu Ser Glu Lys Gln Ala Arg Asp Ile Ala Glu Lys Asp Leu Val Ala
145                 150                 155                 160

Asn Val Thr Lys Glu Val Pro Glu Tyr Glu Gln Gly Lys Asp Thr Glu
                165                 170                 175

Phe Val Val Tyr Val Asn Gly Asp Glu Ala Ser Leu Ala Tyr Val Val
            180                 185                 190

Asn Leu Asn Phe Leu Thr Pro Glu Pro Gly Asn Trp Leu Tyr Ile Ile
        195                 200                 205

Asp Ala Val Asp Gly Lys Ile Leu Asn Lys Phe Asn Gln Leu Asp Ala
    210                 215                 220
```

```
Ala Lys Pro Gly Asp Val Lys Ser Ile Thr Gly Thr Ser Thr Val Gly
225                 230                 235                 240

Val Gly Arg Gly Val Leu Gly Asp Gln Lys Asn Ile Asn Thr Thr Tyr
            245                 250                 255

Ser Thr Tyr Tyr Tyr Leu Gln Asp Asn Thr Arg Gly Asn Gly Ile Phe
            260                 265                 270

Thr Tyr Asp Ala Lys Tyr Arg Thr Thr Leu Pro Gly Ser Leu Trp Ala
        275                 280                 285

Asp Ala Asp Asn Gln Phe Phe Ala Ser Tyr Asp Ala Pro Ala Val Asp
        290                 295                 300

Ala His Tyr Tyr Ala Gly Val Thr Tyr Asp Tyr Tyr Lys Asn Val His
305                 310                 315                 320

Asn Arg Leu Ser Tyr Asp Gly Asn Asn Ala Ala Ile Arg Ser Ser Val
            325                 330                 335

His Tyr Ser Gln Gly Tyr Asn Asn Ala Phe Trp Asn Gly Ser Gln Met
            340                 345                 350

Val Tyr Gly Asp Gly Asp Gly Gln Thr Phe Ile Pro Leu Ser Gly Gly
        355                 360                 365

Ile Asp Val Val Ala His Glu Leu Thr His Ala Val Thr Asp Tyr Thr
    370                 375                 380

Ala Gly Leu Ile Tyr Gln Asn Glu Ser Gly Ala Ile Asn Glu Ala Ile
385                 390                 395                 400

Ser Asp Ile Phe Gly Thr Leu Val Glu Phe Tyr Ala Asn Lys Asn Pro
            405                 410                 415

Asp Trp Glu Ile Gly Glu Asp Val Tyr Thr Pro Gly Ile Ser Gly Asp
            420                 425                 430

Ser Leu Arg Ser Met Ser Asp Pro Ala Lys Tyr Gly Asp Pro Asp His
        435                 440                 445

Tyr Ser Lys Arg Tyr Thr Gly Thr Gln Asp Asn Gly Gly Val His Ile
    450                 455                 460

Asn Ser Gly Ile Ile Asn Lys Ala Ala Tyr Leu Ile Ser Gln Gly Gly
465                 470                 475                 480

Thr His Tyr Gly Val Ser Val Val Gly Ile Gly Arg Asp Lys Leu Gly
            485                 490                 495

Lys Ile Phe Tyr Arg Ala Leu Thr Gln Tyr Leu Thr Pro Thr Ser Asn
            500                 505                 510

Phe Ser Gln Leu Arg Ala Ala Ala Val Gln Ser Ala Thr Asp Leu Tyr
        515                 520                 525

Gly Ser Thr Ser Gln Glu Val Ala
        530                 535
```